(12) United States Patent
Hartmann-Bax et al.

(10) Patent No.: US 11,808,358 B2
(45) Date of Patent: *Nov. 7, 2023

(54) SEALING RING MADE OF A HIGH-PERFORMANCE THERMOPLASTIC MATERIAL AND LIQUID SILICONE

(71) Applicant: BIOTRONIK SE & CO. KG, Berlin (DE)

(72) Inventors: Kathy Hartmann-Bax, Nuthe-Urstromtal (DE); Stefan Lehmann, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/500,371

(22) Filed: Oct. 13, 2021

(65) Prior Publication Data

US 2022/0034405 A1 Feb. 3, 2022

Related U.S. Application Data

(63) Continuation of application No. 16/568,553, filed on Sep. 12, 2019, now Pat. No. 11,174,942.

(30) Foreign Application Priority Data

Sep. 12, 2018 (EP) .................................... 18194056

(51) Int. Cl.
| | | |
|---|---|---|
| *F16J 15/3284* | (2016.01) | |
| *F16J 15/10* | (2006.01) | |
| *A61N 1/375* | (2006.01) | |
| *F16J 15/44* | (2006.01) | |

(52) U.S. Cl.
CPC ........ *F16J 15/3284* (2013.01); *A61N 1/3752* (2013.01); *F16J 15/104* (2013.01); *F16J 15/442* (2013.01)

(58) Field of Classification Search
CPC ...... F16J 15/3284; F16J 15/104; F16J 15/442; A61N 1/3752
See application file for complete search history.

(56) References Cited

U.S. PATENT DOCUMENTS

| | | | |
|---|---|---|---|
| 7,299,095 B1 * | 11/2007 | Barlow | A61N 1/3752 607/36 |
| 7,367,973 B2 | 5/2008 | Manzo et al. | |
| 8,167,660 B2 * | 5/2012 | Dilmaghanian | H01R 13/5219 439/669 |

(Continued)

FOREIGN PATENT DOCUMENTS

| | | |
|---|---|---|
| CN | 205350358 U | 6/2016 |
| EP | 2740516 A2 | 6/2014 |
| RU | 2179274 C1 | 2/2002 |

*Primary Examiner* — Gilbert Y Lee
(74) *Attorney, Agent, or Firm* — Laurence A. Greenberg; Werner H. Stemer; Ralph E. Locher

(57) ABSTRACT

A sealing ring for a header of an implantable device has an outer ring and an inner ring. The outer ring is formed with, or of, a high-performance thermoplastic material. The inner ring is formed with, or of, liquid silicone or polyurethane. The inner and outer rings are arranged with a form-fit relative to each other. There is also described a method for manufacturing such a sealing ring and also a contact socket and an implantable device with such a sealing ring.

8 Claims, 4 Drawing Sheets

(56) References Cited

U.S. PATENT DOCUMENTS

| | | | |
|---|---|---|---|
| 8,666,494 B2* | 3/2014 | Schramm | A61N 1/3752 |
| | | | 607/37 |
| 8,751,002 B2 | 6/2014 | Kast et al. | |
| 2003/0163171 A1* | 8/2003 | Kast | A61N 1/3752 |
| | | | 607/36 |
| 2004/0122481 A1 | 6/2004 | Tidemand et al. | |
| 2008/0177167 A1 | 7/2008 | Janzig et al. | |
| 2009/0017668 A1 | 1/2009 | Deininger et al. | |
| 2011/0059639 A1 | 3/2011 | Dilmaghanian et al. | |
| 2015/0018909 A1 | 1/2015 | Rebentisch et al. | |
| 2016/0184594 A1 | 6/2016 | Baade et al. | |

* cited by examiner

SEALING RING MADE OF A HIGH-PERFORMANCE THERMOPLASTIC MATERIAL AND LIQUID SILICONE

CROSS-REFERENCE TO RELATED APPLICATION

This application claims the priority, under 35 U.S.C. § 120, of co-pending patent application Ser. No. 16/568,553, filed Sep. 12, 2019; the application also claims the priority, under 35 U.S.C. § 119, of European patent application EP 18194056, filed Sep. 12, 2018; the prior applications are herewith incorporated by reference in their entirety.

BACKGROUND OF THE INVENTION

Field of the Invention

The present invention relates to a sealing ring, in particular for use in a connection head (header) of an implantable device, and to a method for manufacturing the sealing ring.

Insulating sealing elements in pluggable contact sockets in connection heads or headers of implantable devices are known in the prior art. The header is used here in particular to conduct electrical pulses from the core of the implantable device to an electrode lead that is plugged into the header, and also possibly in the reverse direction. The parts of the header, in particular the contact socket, are typically cast into a block of epoxy resin so as to be protected against the influences of the target environment. The aforementioned sealing elements are intended to ensure in particular electrical insulation between the electrically conductive contacts in the header. Furthermore, such seal elements can be used as an attachment surface for the above-mentioned epoxy resin and so as to produce a certain distance between the electrically conductive contacts.

By way of example, published patent application US 2008/0177167 A1 discloses insulating sealing elements in pluggable contact sockets, which consist of a core that is used to ensure the distance between two electrical contacts, as a stop for the assembly process, as an attachment surface for joining materials, and for mechanical fixing of a seal ("wiper seal"). The disclosed materials for this core are polycrystalline materials, single crystals, and crystalline sapphire.

The general structure of pluggable contact sockets in medical implants is disclosed for example in published patent application US 2015/0018909 A1, in U.S. Pat. No. 8,751,002 B2 or in published patent application US 2009/0017668 A1.

Furthermore, published patent application US 2011/0059639 A1 describes the use of silicone for sealing and for electrical insulation in respect of contact sockets for medical implants. Published patent application US 2009/0017668 A1 discloses the use of liquid silicone rubber (LSR) for insulating sealing elements in pluggable contact sockets.

Nevertheless, there is still a need for suitable designs for such sealing elements which fulfil the above-mentioned objectives to the best-possible extent.

SUMMARY OF THE INVENTION

Against this background it is an object of the invention to provide a sealing ring and a manufacturing method which overcome the above-mentioned and other disadvantages of the heretofore-known devices and methods of this general type and which provide improved sealing elements and methods for the manufacture thereof.

With the foregoing and other objects in view there is provided, in accordance with the invention, a sealing ring for a header of an implantable device, the sealing ring comprising:

an outer ring formed with, or consisting essentially of, a high-performance thermoplastic material being a polyaryl or a liquid-crystal polymer, with the polyaryl being selected from the group consisting of a poly(aryl ether sulfone), a polyaryletherketone, and a polyphenylene sulfide; and an inner ring formed with, or consisting essentially of, a liquid silicone or a polyurethane;

wherein said inner ring and said outer ring are arranged with a form fit relative to one another.

In other words, the objects of the invention are achieved with a sealing ring for use in a header of an implantable device is provided. The sealing ring according to the invention comprises the following components: an outer ring or core comprising or essentially consisting of a high-performance thermoplastic material, and an inner ring comprising or essentially consisting of a liquid silicone or a polyurethane. The inner ring and the outer ring are arranged with a form-fitting, or positive, engagement into one another.

In accordance with the invention it is particularly provided that the high-performance thermoplastic material is selected from the group comprising a polyaryl and a liquid-crystal polymer, wherein the polyaryl is selected in particular from a poly(aryl ether sulfone), a polyaryletherketone and a polyphenylene sulfide.

The term "liquid-crystal polymer" is used in the context of the present specification in the sense known and familiar to a person skilled in the art. A "liquid-crystal polymer" in particular denotes an aromatic polymer that has highly ordered or crystalline areas in the melt or in solution. Non-limiting examples include aromatic polyamides such as aramid (Kevlar) and aromatic polyesters such as a polycondensate formed from 4-hydroxybenzoic acid and 6-hydroxynaphthalene-2-carboxylic acid (Vectran).

The term polysulfone or poly(aryl ether sulfone) in the context of the present specification particularly refers to a thermoplastic material with an aryl-$SO_2$-aryl sub-unit. Non-limiting examples of polysulfones and poly(aryl ether sulfone) include polysulfone (CAS No. 25135-51-7), poly (arylene sulfone), poly(bisphenyl sulfone) (CAS No. 25135-51-7), Victrex HTA (CAS No. 121763-41-5), polyether sulfone (CAS No. 25608-63-3) and polyphenylene sulfone (CAS No. 25608-64-4).

In the context of the present specification, a thermoplastic material with an aryl-O-aryl-C(O)-aryl sub-unit, that is to say aryl groups which are always linked to one another alternately via a keto group (—C(O)— and an ether group (—O—), is referred to as poly(aryl ether ketone). A non-limiting example is polyether ether ketone (PEEK, CAS No. 29658-26-2).

In the context of the present specification, a thermoplastic material with an aryl-S-aryl sub-unit, that is to say aryl groups which are each linked to one another via a sulfide group (—S—), is referred to as a polyphenyl sulfide. A non-limiting example is poly(thio-p-phenylene) (CAS No. 26125-40-6, 25212-74-2).

The above-mentioned polyaryls and the liquid-crystal polymer advantageously enable an efficient attachment to resins, for example epoxy, which typically are used in headers of implantable medical devices.

In particular, a thermoplastic elastomer which not only comprises poly(organo)siloxanes, but also cross-linkable groups such as vinyl groups and Si—H groups, which typically are added in a noble-metal-catalysed reaction, is referred to as liquid silicone or liquid-silicone rubber in the context of the present specification. In addition, the liquid silicone may comprise additives, such as reinforcing substances and/or fillers.

Preferably, the polyurethane is a thermoplastic or elastic (elastomer) polyurethane.

In some embodiments of the sealing ring according to the invention, the inner ring forms at least one groove, wherein the groove has a base and two opposite sides, which extend from the base, and the outer ring engages in the groove in a form-fit manner.

In some embodiments of the sealing ring according to the invention, the outer ring has at least one aperture, in particular a slot, and the inner ring has at least one bar, which extends from one side of the groove to the other side of the groove, and the at least one bar passes through the at least one aperture.

In some embodiments of the sealing ring according to the invention, the outer ring has two or more apertures or slots, in particular 3 apertures or slots, and the inner ring has two or more bars accordingly, in particular 3 bars, wherein the two or more bars pass through one of the two or more apertures, respectively.

In some embodiments of the sealing ring according to the invention, the outer ring is injection molded.

In some further embodiments of the sealing ring according to the invention, the inner ring is injection molded.

In some further embodiments of the sealing ring according to the invention, the inner ring is injection molded around the outer ring. If the outer ring has at least one aperture, the at least one bar of the inner ring is advantageously formed in this way and engages through the at least one aperture in the outer ring, and the outer ring and the inner ring are arranged to each other in a form-fit manner.

In some embodiments of the sealing ring according to the invention, the liquid silicone is selected from a two-component mixture of any Shore hardness, which is biocompatible. In accordance with one exemplary embodiment, the components may be selected from the group SILASTIC® BioMedical Grade Liquid Silicone Rubbers (Dow Corning Corporation) or Silpuran 6600 (Wacker Chemie AG).

In accordance with a further feature of the invention, there is provided a contact socket for an implantable medical device, in particular for a connection head of an implantable medical device. The contact socket comprises at least one sealing ring of the invention as outlined, or one of the previously described embodiments of the sealing ring of the invention.

Particularly, an assembly of an implantable medical device that ensures an electrical connection between a current-generating or current-emitting component (generator component, battery) or a current-detecting component (diagnosis component) of an implantable device and an electrode lead is referred to as a connection head or header in the context of the present specification.

In particular, the contact socket according to the invention comprises a plurality of electrical contacts, wherein a sealing ring according to the invention is arranged between each two electrical contacts. The plurality of electrical contacts and the sealing rings arranged in-between form a cavity, in particular a cylindrical cavity, which is designed to receive a plug of an electrode lead. Furthermore, the electrical contacts are designed to transfer or receive electrical currents or pulses to/from the plug of the electrode lead. The electrical contacts for this purpose are typically in contact with a current-generating or current-emitting component (generator component, battery) or a current-detecting component (diagnosis component).

The electrical contacts of the contact socket according to the invention are preferably spring contacts. The contact socket may also comprise a plug receptacle or socket (connector block) with threaded pin at the end or at the start of the contact socket. Such plug receptacles or sockets, similarly to the spring contacts, may be electrically insulated and sealed by a sealing ring according to the invention.

The contact socket according to the invention is also preferably cast into a block of a thermosetting plastic, wherein a connection head is thus formed. The thermosetting plastic is preferably a transparent plastic, particularly an epoxy resin.

With the above and other objects in view there is also provided, in accordance with the invention, an implantable medical device, which comprises at least one sealing ring as described in any of the embodiments or a contact socket as described in any of the embodiments.

The implantable medical device is in particular a cardiac pacemaker, a cardioverter-defibrillator, or a neurostimulator, such as a spinal cord stimulator.

The implantable cardioverter-defibrillator (ICD) is in particular a device that has a stimulation part (pulse generator) and a diagnostics part (for identifying dangerous rhythm disturbances), wherein the stimulation/diagnostics part, usually implanted under the skin in the vicinity of the left pectoral muscle, is connected to the right ventricle via an electrode lead. The electrode lead is guided here into the right heart chamber typically via the superior vena cava.

The spinal cord stimulator is in particular a device for the treatment of chronic neuropathic pain, in which a pulse generator is connected via an electrode lead to the part of the nervous system to be treated, for example to the posterior column of the spinal cord.

The implantable medical device typically has a housing formed from a resistant, biocompatible material, preferably titanium or a titanium alloy, wherein device components, which are necessary for the intended use of the device, for example control units, power sources, pulse generators or diagnosis units, are arranged in the housing.

With the above and other objects in view there is also provided, in accordance with the invention, a method for producing a sealing ring, in particular the sealing ring as described. The method comprises the following steps:

providing an outer ring comprising or essentially consisting of a high-performance thermoplastic material, providing an inner ring comprising or essentially consisting of a liquid-silicone or a polyurethane, and arranging the outer ring and the inner ring to each other in a form-fit manner.

In accordance with the invention, it is provided in particular that the high-performance thermoplastic material is selected from the group comprising a polyaryl and a liquid-crystal polymer, wherein the polyaryl is selected in particular from a poly(aryl ether sulfone), a poly(aryl ether ketone) and a polyphenylene sulfide.

In some embodiments of the method according to the invention, the inner ring forms at least one groove, wherein the groove has a base and two opposite sides, which extend from the base, and the outer ring engages in the groove in a form-fit manner.

In some embodiments of the method according to the invention, the outer ring has at least one aperture, in particular a slot, and the inner ring has at least one bar, which extends from one side of the groove to the other side of the groove, and the at least one bar passes through the at least one aperture.

In some embodiments of the method according to the invention, the outer ring is provided by an injection molding process, wherein in particular the outer ring is polished or cleaned after the injection molding.

In some embodiments of the method according to the invention, the inner ring is provided by an injection molding process.

In some embodiments of the method according to the invention, the inner ring is injection molded around the outer ring and is arranged to the outer ring in a form-fit manner.

In some embodiments of the method according to the invention, the outer ring is pre-treated prior to being arranged in a form-fit manner, in particular prior to being overmolded by the inner ring, in particular with use of a plasma or an adhesion promoter (primers).

Other features which are considered as characteristic for the invention are set forth in the appended claims.

Although the invention is illustrated and described herein as embodied in sealing ring made of a high-performance thermoplastic material and liquid silicone, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1A:
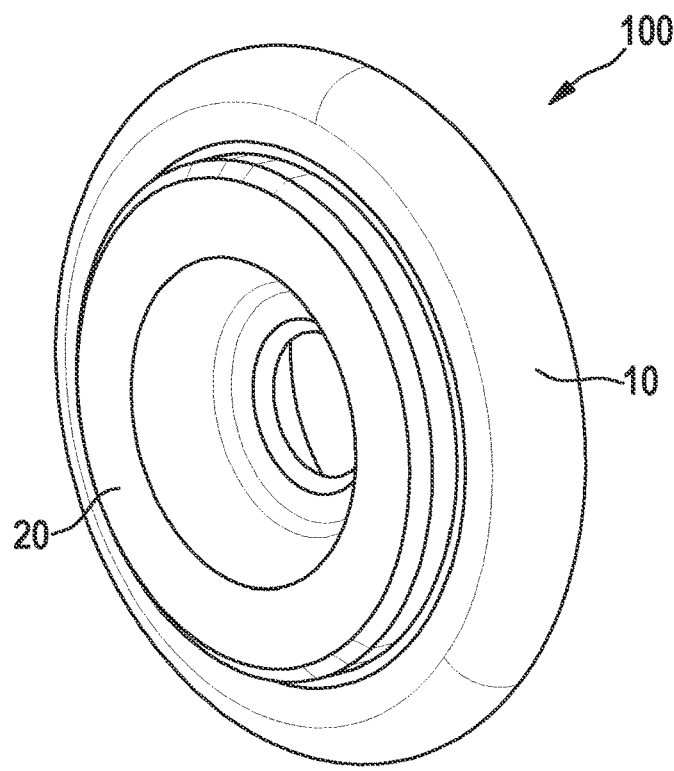
FIG. 1A and FIG. 1B show perspective, schematic views of an embodiment of the sealing ring according to the invention.
Figure 1B:
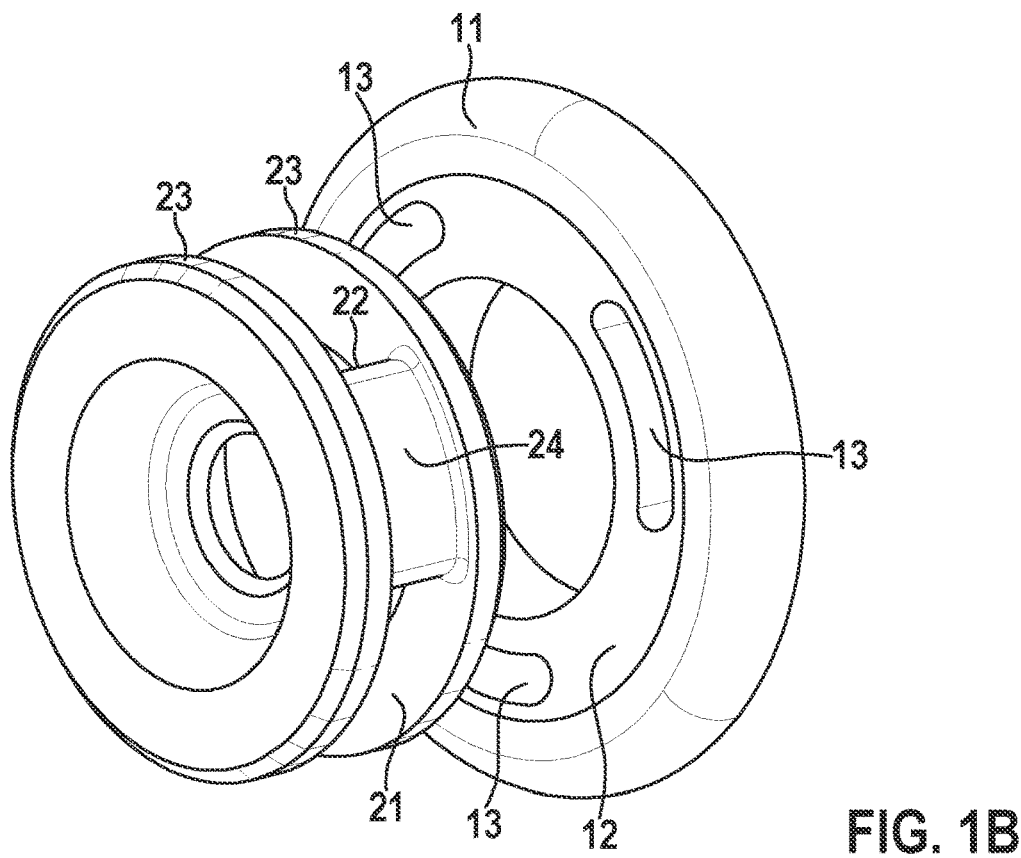

Referring now to the figures of the drawing in detail and first, particularly, to FIGS. 1A and 1B thereof, the present invention relates in particular to a sealing element 100 made of a PSU component 10 and an overmolding 20 made of LSR (liquid silicone rubber). The PSU component is designed here in particular as an outer ring 10, and the LSR overmolding is designed as an inner ring 20.

The PSU core 10 performs the following functions and has the following advantages:
distance between 2 electrical contacts
limit stop for the assembly process
attachment surface for resin for forming the header
mechanical fixing to the silicone (apertures)
attachment surface for silicone possibly for plasma processes or primer The LSR overmolding 20 performs the following functions and has the following advantages:
electrical insulation between two electrical contacts (provided by spherical end-face sealing surfaces of the inner ring, which leads to a form-fit connection between the electrical contacts, when the contact socket is clamped)
potential separation between electrode and cavity
seal against infiltration of resin during the resin casting (realised by the defined limit stop surface and resultant technical zero gap between the PSU rim and the housing of the electrical contact).

These constitute three independent sealing functions.

FIG. 1A illustrates an embodiment of the sealing ring 100 according to the invention which consists of an outer ring 10 made of PSU and an inner ring 20 made of a liquid silicone or liquid-silicone rubber. FIG. 1B shows a detailed view of the outer ring 10 and of the inner ring 20. The outer ring 10 has slots 13 (apertures), which are used to grip or claw the inner ring 20 made of LSR. The inner ring 20 in turn forms a groove 21, which comprises a base 22 and two opposite walls, which extend from the base. The outer ring advantageously has 2 or 3 bars, which extend from a wall 23 of the groove 21 to the other wall 23 of the groove 21. These bars 24 each pass through a corresponding slot in the outer ring 10 and thus ensure a form-fit connection between the inner ring 20 and outer ring 10.

The outer ring 10 is used in particular as a limit stop for assembly of the electrical contacts 30. Due to the used PSU, a particularly good attachment to the epoxy resin that is used during course of manufacture of the header is possible, and this thus contributes to the electrical insulation above the PSU core. In addition, the outer ring serves as a guide for the wiring ribbons between the electrical contacts 30, for example of an 8-pole module, an an electrical feedthrough to the interior of the housing. This assists the process in which the wiring ribbons are welded onto the electrical contact 30. By design, an potential separation of the wiring ribbons is thus also realised.

Figure 2:
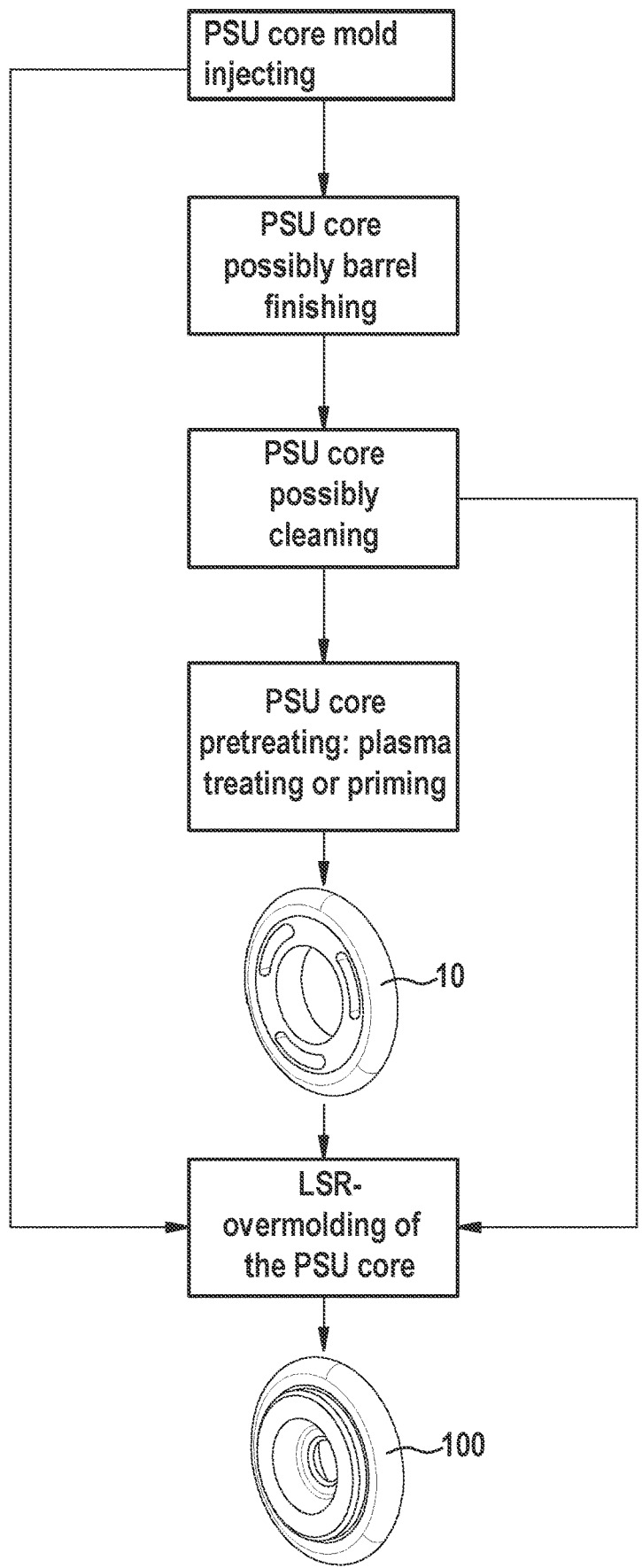
FIG. 2 shows a schematic view of an embodiment of the production method according to the invention.

FIG. 2 shows a flowchart that outlines the manufacture of the sealing ring 100 according to the invention. The PSU core or outer ring 10 is firstly provided by an injection molding process. As appropriate, the outer ring 10 is pre-treated by a vibratory finishing (barrel finishing) or by a cleaning process. The outer ring 10 is preferably additionally plasma-treated or primed (treatment with an adhesion promoter) to provide improved adhesion of the LSR 20. LSR is then injection-molded around the outer ring 10, wherein the LSR then forms the inner ring 20. If the outer ring 10 has slots 13, these are filled by the LSR, wherein an inner ring 20 with groove 21 and bars 24 is thus formed, wherein the bars 24 then pass through the corresponding slots 13, and a form-fit connection is formed between outer ring 10 and inner ring 20.

Figure 3A:
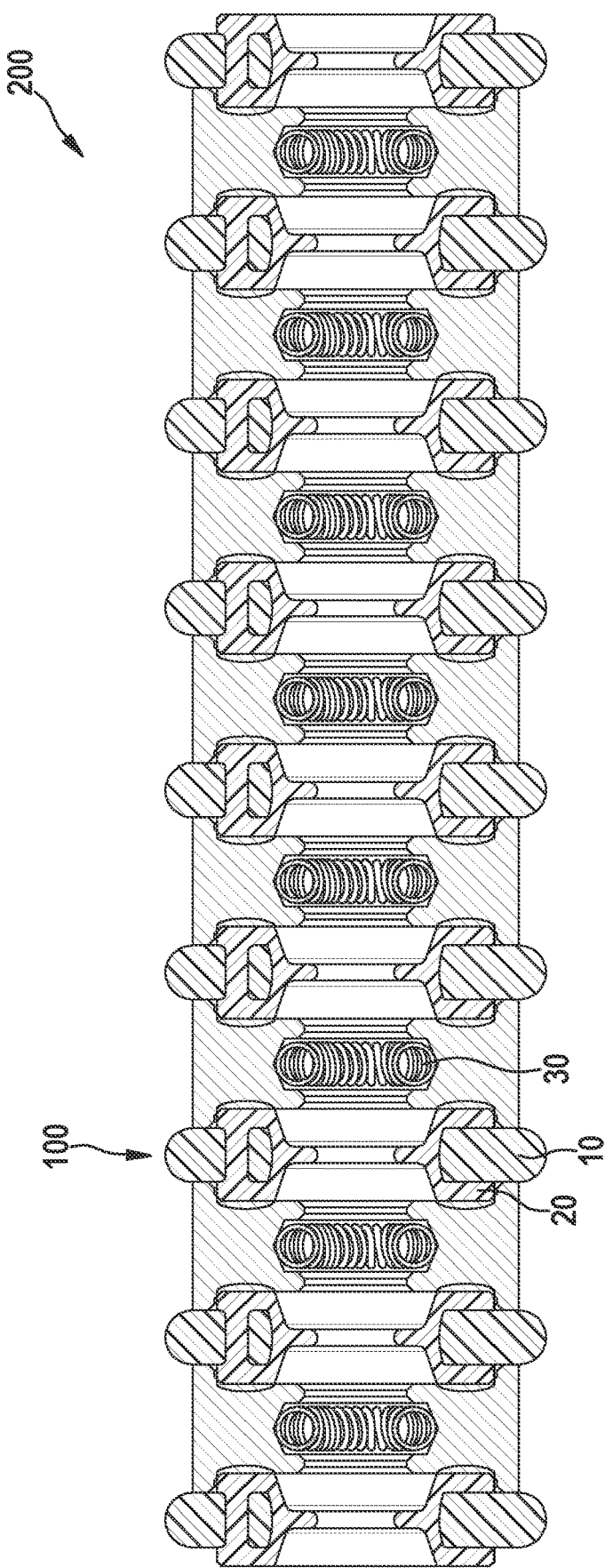
FIG. 3A and FIG. 3B are sectional views of an embodiment of the contact socket according to the invention.
Figure 3B:
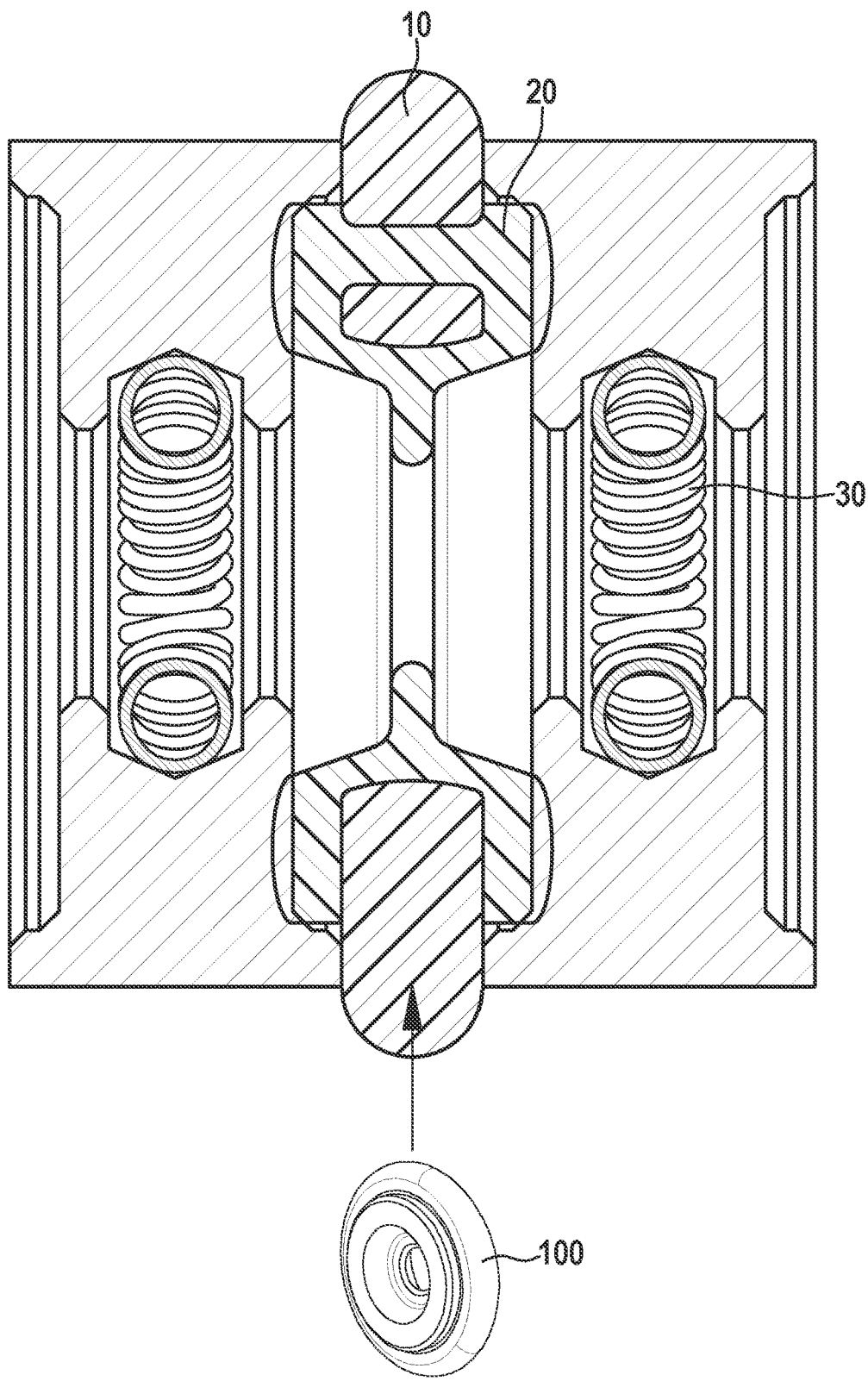

FIG. 3A shows schematic sectional view of a contact socket 200 according to the invention, with FIG. 3B showing an enlarged partial view. The contact socket has a plurality of electrical contacts 30, in particular spring contacts, between each two of which a sealing ring 10 according to the invention is arranged. The contact socket 200 has a cavity in its interior, in particular a cylindrical cavity, which is designed to receive a plug of an electrode lead. Here, the electrical contacts 30 are used to conduct a current or electrical pulse between the plug of the electrode lead and the current-emitting or current-detecting components of an implantable device (for example ICD), which are accommodated in the housing of the device. The electrical contacts 30 are connected to the interior of the housing in particular via wiring ribbons.

In order to provide the liquid silicone, the components A and B, the 40 Shore Material LSR Silastic 7-6840 (Dow Corning Corporation), were mixed with one another in a ratio of 1:1 and were annealed or tempered to provide an improved final cross-linking of the silicone material in a circulating air furnace (=post cure process). In principle, however, other Shore hardnesses of the LSR Silastic product family are also suitable, for example 30, 50 or 60. The temperature of the tempering is dependent in particular on the material of the core, in particular on its melting point or glass transition temperature. In the case of a PSU core 10, tempering is performed at a temperature of approximately 150° C. for 12 hours. In the case of a PEEK core 10 higher temperatures may be used. Alternatively, liquid silicones of the Silpuran 6600 product family with Shore hardnesses between 40 and 60 can also be used.

The invention claimed is:

1. A contact socket for an implantable medical device, the contact socket comprising:
   a plurality of electrical contacts; and
   at least one sealing ring having:
      an outer ring formed with, or consisting essentially of, a high-performance thermoplastic material being a polyaryl or a liquid-crystal polymer, with the polyaryl being selected from the group consisting of a poly(aryl ether sulfone), a polyaryletherketone, and a polyphenylene sulfide; and
      an inner ring formed with, or consisting essentially of, a liquid silicone or a polyurethane;
   said inner ring and said outer ring being arranged with a form fit relative to one another;
   said at least one sealing ring being arranged between two electrical contacts of the plurality of electrical contacts; and
   said outer ring having a larger diameter than said two electrical contacts, and said inner ring having a smaller diameter than said two electrical contacts.

2. The implantable device according to claim 1, wherein said inner ring is formed with at least one groove having a base and two opposite sides that extend from said base, and said outer ring engages in said groove with a form-fit engagement.

3. The implantable device according to claim 2, wherein said outer ring is formed with at least one aperture and said inner ring has at least one bar, which extends from one side of said groove to the other side of the groove, and said at least one bar passes through said at least one aperture.

4. The implantable device according to claim 3, wherein said at least one aperture formed in said outer ring is a slot.

5. The implantable device according to claim 1, wherein said liquid silicone is selected from a two-component mixture of any Shore hardness which is biocompatible.

6. The implantable device according to claim 1, wherein said outer ring is an injection-molded element.

7. The implantable device according to claim 1, wherein said inner ring is injection-molded around said outer ring.

8. An implantable device, comprising a contact socket according to claim 1, and being an implantable cardioverter-defibrillator or an implantable spinal cord stimulator.

* * * * *